(12) United States Patent
Zeun et al.

(10) Patent No.: US 6,306,888 B1
(45) Date of Patent: Oct. 23, 2001

(54) MICROBICIDES

(75) Inventors: Ronald Zeun, Neuenburg; Gertrude Knauf-Beiter, Müllheim, both of (DE)

(73) Assignee: Syngenta Investment Corporation, Wilmington, DE (US)

( * ) Notice: Subject to any disclaimer, the term of this patent is extended or adjusted under 35 U.S.C. 154(b) by 0 days.

(21) Appl. No.: 09/290,741

(22) Filed: Apr. 13, 1999

Related U.S. Application Data

(62) Division of application No. 08/735,040, filed on Oct. 22, 1996, now Pat. No. 5,929,102, which is a division of application No. 08/443,942, filed on May 18, 1995, now Pat. No. 5,599,828.

(30) Foreign Application Priority Data

May 20, 1994 (CH) ................................. 1576/94-5

(51) Int. Cl.$^7$ .................................. A01N 43/64
(52) U.S. Cl. ............................................. 514/383
(58) Field of Search ............................... 514/383

(56) References Cited

U.S. PATENT DOCUMENTS

| | | |
|---|---|---|
| 4,906,652 | 3/1990 | Karbeck et al. ....................... 514/383 |
| 4,911,746 | 3/1990 | Holmwood et al. ....................... 71/92 |
| 4,931,560 | 6/1990 | Hubele ................................. 544/315 |
| 5,210,198 | 5/1993 | Debourge et al. ................ 548/268.8 |
| 5,250,559 | 10/1993 | Mittermeiser et al. ............... 514/383 |
| 5,403,844 | 4/1995 | Mittermeiser et al. ............... 514/275 |

FOREIGN PATENT DOCUMENTS

| | | |
|---|---|---|
| 0234242 | 9/1987 | (EP) . |
| 0251775 | 1/1988 | (EP) . |
| 0267778 | 5/1988 | (EP) . |
| 0393746 | 10/1990 | (EP) . |
| 1522657 | 8/1978 | (GB) . |
| 2264641 | 9/1993 | (GB) . |
| 2267644 | 12/1993 | (GB) . |
| 96/01054 | 1/1996 | (WO) . |

*Primary Examiner*—Allen J. Robinson
(74) *Attorney, Agent, or Firm*—William A. Teoli, Jr.

(57) ABSTRACT

A plant-microbicidal composition having synergistic action, comprising at least two active ingredient components, wherein component I is a compound selected from the group (IA) 1-[3-(2-chlorophenyl)-2-(4-fluorophenyl)oxiran-2-ylmethyl]-1H-1,2,4-triazole ("epoxiconazol");

(IB) 4-(4-chlorophenyl)-2-phenyl-2-(1,2,4-triazol-1-ylmethyl)-butyronitrile ("fenbuconazol");

(IC) 5-(4-chlorobenzyl)-2,2-dimethyl-1-(1H-1,2,4-triazol-1-ylmethyl)-cyclopentanol ("metconazol");

(ID) 2-(2,4-dichlorophenyl)-3-(1H-1,2,4-triazol-1-yl) propyl-1,1,2,2-tetrafluoroethyl ether ("tetraconazol");

(IE) α-[2-(4-chlorophenyl)ethyl]-α-(1,1-dimethylethyl)-1H-1,2,4-triazole-1-ethanol ("tebuconazol");

(IF) 1-[4-bromo-2-(2,4-dichlorophenyl) tetrahydrofurfuryl]-1H-1,2,4-triazole ("bromuconazol");

or in each case one of the salts or metal complexes thereof; and component II is (IIA) 1-[2-(2,4-dichlorophenyl)-4-propyl-1,3-dioxolan-2-ylmethyl]-1H-1,2,4-triazole ("propiconazol") and/or (IIB) 4-cyclopropyl-6-methyl-N-phenyl-2-pyrimidineamine ("cyprodinil"), or in each case one of the salts or metal complexes thereof.

5 Claims, No Drawings

MICROBICIDES

This application is a divisional application of U.S. Ser. No. 08/735,040, filed Oct. 22, 1996, now U.S. Pat. No. 5,929,102, which is a divisional of U.S. Ser. No. 08/443,942, filed May 18, 1995, now U.S. Pat. No. 5,599,828, which claims priority from Swiss application 1576/94-5, filed May 20, 1994.

The present invention relates to novel microbicidal active ingredient mixtures having synergistically enhanced action, comprising at least two active ingredient components, and to methods of using such mixtures in plant protection.

Component I is a compound selected from the group:

(IA) 1-[3-(2-chlorophenyl)-2-(4-fluorophenyl)oxiran-2-ylmethyl]-1H-1,2,4-triazole ("epoxiconazol"; reference: EP-A-196 038);

(IB) 4-(4-chlorophenyl)-2-phenyl-2-(1,2,4-triazol-1-ylmethyl)-butyronitrile ("fenbuconazol"; reference: EP-A-251 775);

(IC) 5-(4-chlorobenzyl)-2,2-dimethyl-1-(1H-1,2,4-triazol-1-ylmethyl)-cyclopentanol ("metconazol"; reference: EP-A-267 778);

(ID) 2-(2,4-dichlorophenyl)-3-(1H-1,2,4-triazol-1-yl)propyl-1,1,2,2-tetrafluoroethyl ether ("tetraconazol"; reference: EP-A-234 242);

(IE) α-[2-(4-chlorophenyl)ethyl]α-(1,1-dimethylethyl)-1H-1,2,4-triazole-1-ethanol ("tebuconazol"; reference: EP-A-40 345);

(IF) 1-[4-bromo-2-(2,4-dichlorophenyl)tetrahydrofurfuryl]-1H-1,2,4-triazole ("bromuconazol"; reference EP-A-246 982), or in each case one of the salts or metal complexes thereof; and component II is the compound:

(IIA) 1-[2-(2,4-dichlorophenyl)-4-propyl-1,3-dioxolan-2-ylmethyl]-1H-1,2,4-triazole ("propiconazol"; reference: GB-1 522 657) and/or (IIB) 4-cyclopropyl-6-methyl-N-phenyl-2-pyrimidineamine ("cyprodinil"; reference: EP-A-310 550)

or in each case one of the salts or metal complexes thereof.

Of the acids that can be used for the preparation of salts of compounds of formulae I and II, the following may be mentioned:

hydrohalic acids, such as hydrofluoric acid, hydrochloric acid, hydrobromic acid or hydriodic acid; sulfuric acid, phosphoric acid, nitric acid; and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid and 1,2-naphthalene-disulfonic acid.

The term salts also includes metal complexes of basic components I and II. Those complexes may as desired involve only one component or both components independently. It is also possible to produce metal complexes in which the two active ingredients I and II are linked to one another to form a mixed complex.

Metal complexes consist of the underlying organic molecule and an inorganic or organic metal salt, for example a halide, nitrate, sulfate, phosphate, acetate, trifluoroacetate, trichloroacetate, propionate, tartrate, sulfonate, salicylate, benzoate, etc., of an element of main group II, such as calcium and magnesium, and of main groups III and IV, such as aluminium, tin or lead, and of subgroups I to VIII, such as chromium, manganese, iron, cobalt, nickel, copper, zinc, etc. Preference is given to the subgroup elements of the 4th period. The metals may have any of the different valencies in which they occur. The metal complexes can be mono- or poly-nuclear, i.e. they can contain one or more organic molecule components as ligands.

Further agrochemical active ingredients, such as insecticides, acaricides, nematicides, herbicides, growth regulators and fertilisers, but especially additional microbicides, may also be added to the active ingredient mixture according to the invention.

Synergistic mixtures are known wherein a) component I is compound IA ("epoxiconazol") and component II is compound IIB ("cyprodinil");

b) component I is compound IB ("fenbuconazol") and component II is compound IIB ("cyprodinil");

c) component I is compound IE ("tebuconazol") and component II is compound IIB ("cyprodinil") (reference for a), b) and c): EP-A-548 025); and d) component I is compound IE ("tebuconazol") and component II is compound IIA ("propiconazol") (reference: EP-A-393 746).

The present invention does not relate to those mixtures.

It has now been found, surprisingly, that the fungicidal action of mixtures according to the invention of components I and II is not merely additive but is clearly synergistically enhanced.

Preference is given to two-component mixtures wherein (1) component I is a compound selected from the group IA ("epoxiconazol"), IB ("fenbuconazol"), IC ("metconazol"), ID ("tetraconazol") and IE ("tebuconazol"); and component II is compound IIA ("propiconazol") and/or IIB ("cyprodinil");

(2) component I is a compound selected from the group IA ("epoxiconazol"), IB ("fenbuconazol"), IC ("metconazol"), ID ("tetraconazol") and IF ("bromuconazol"); and component II is compound IIA ("propiconazol");

(3) component I is a compound selected from the group IC ("metconazol"), ID ("tetraconazol") and IF ("bromuconazol"); and component II is compound IIB ("cyprodinil").

(4) A further preferred group is formed by three-component mixtures wherein component I is a compound selected from the group IA ("epoxiconazol"), IB ("fenbuconazol"), IC ("metconazol"), ID ("tetraconazol"), IE ("tebuconazol") and IF ("bromuconazol"); and component II is a mixture of IIA ("propiconazol") and IIB ("cyprodinil") and the ratio by weight of IIA:IIB=1:6 to 6:1.

(5) Of the above, preference is given especially to three-component mixtures wherein component I is compound IE ("tebuconazol") and component II is a mixture of IIA ("propiconazol") and IIB ("cyprodinil").

The present invention relates also to a method of controlling fungi which comprises treating a site infested by or threatened with infestation by fungi with, in any desired sequence or simultaneously, a) a compound of formula I or one of the salts thereof and b) the compound of formula II or one of the salts thereof, it being possible also for the salts to be so selected that the two compounds are bonded to an acid radical or, in the case of a metal complex, to a central metal cation.

Advantageous mixing ratios of the two compounds are I:II=1:10 to 10:1, preferably I:II=1:6 to 6:1 and especially I:II=1:3 to 3:1. Other advantageous mixing ratios I:II are, for example, 1:1, 1:2, 1:4, 2:1, 2:3.

In the three-component mixtures, preferred mixing ratios IIA:IIB for component II=1:6 to 6:1 and especially 1:5 to 1:1.

The compound mixtures I+II according to the invention have very advantageous curative, preventive and systemic fungicidal properties for protecting plants. The compound mixtures of the invention can be used to inhibit or to destroy the microorganisms occurring on plants or on parts of plants (the fruit, blossom, leaves, stems, tubers or roots) of different crops of useful plants, while at the same time parts of plants that grow later are also protected against such microorganisms. They can also be used as dressings in the treatment of plant propagation material, especially seed (fruit, tubers, grains) and plant cuttings (for example rice), to provide protection against fungal infections and against phytopathogenic fungi occurring in the soil. The compound mixtures according to the invention are distinguished by the fact that they are especially well tolerated by plants and are environmentally friendly.

The compound mixtures are effective against phytopathogenic fungi belonging to the following classes: Ascomycetes (e.g. Venturia, Podosphaera, Erysiphe, Monilinia, Uncinula); Basidiomycetes (e.g. the genera Hemileia, Rhizoctonia, Puccinia); Fungi imperfecti (e.g. Botrytis, Helminthosporium, Rhynchosporium, Fusarium, Septoria, Cerco-spora, Alternaria, Pyricularia and Pseudocercosporella herpotrichoides); and Oomycetes (e.g. Phytophthora, Peronospora, Bremia, Pythium and Plasmopara).

Target crops to be protected within the scope of the present invention comprise, for example, the following species of plants: cereals: (wheat, barley, rye, oats, rice, sorghum and related species); beets: (sugar beet and fodder beet); pomes, stone fruit and soft fruit: (apples, pears, plums, peaches, almonds, cherries, strawberries, raspberries and black-berries); leguminous plants: (beans, lentils, peas and soybeans); oil plants: (rape, mustard, poppy, olives, sunflowers, coconut, castor oil plants, cocoa beans and groundnuts); cucumber plants: (marrows, cucumber and melons); fibre plants: (cotton, flax, hemp and jute); citrus fruit: (oranges, lemons, grapefruit and mandarins); vegetables: (spinach, lettuce, asparagus, cabbages, carrots, onions, tomatoes, potatoes and paprika); lauraceae: (avocados, cinnamon and camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). That list does not represent any limitation.

The compound mixtures according to the invention are especially advantageous for applications in cereals, especially in wheat and barley.

The mixtures of compounds of formulae I and II are generally used in the form of compositions. The compounds of formulae I and II can be applied to the area or plant to be treated, either simultaneously or in succession on the same day, together with, where appropriate, further carriers, surfactants or other application-promoting adjuvants customarily employed in formulation technology.

Suitable carriers and adjuvants may be solid or liquid and are substances ordinarily employed in formulation technology, for example natural or regenerated mineral substances, solvents, dispersants, wetting agents, tackifiers, thickeners, binders or fertilisers.

A preferred method of applying a compound mixture comprising at least one of each of compounds I and II is application to the parts of the plants that are above the soil, especially to the leaves (foliar application). The frequency and rate of application depend on the biological and climatic living conditions of the pathogens. The compounds can, however, also penetrate the plants through the roots via the soil (systemic action) if the locus of the plant is impregnated with a liquid formulation (for example in rice culture), or if the compounds are introduced in solid form into the soil, e.g. in the form of granules (soil application). In order to treat the seed, the compounds of formulae I and II may also be applied to the seeds (coating) either by impregnating the tubers or grains with a liquid formulation of each of the compounds in succession or by coating them with an already combined wet or dry formulation. In addition, in special cases, other methods of application to plants are possible, e.g. treatment directed at the buds or the fruit.

The compounds of the combination are used in unmodified form or preferably together with the adjuvants conventionally employed in formulation technology, and are therefore formulated in known manner, e.g. into emulsifiable concentrates, coatable pastes, directly sprayable or dilutable solutions, dilute emulsions, wettable powders, soluble powders, dusts or granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the active ingredient mixture are generally from 50 g to 2 kg a.i./ha, preferably from 100 g to 1000 g a.i./ha, especially from 400 g to 1000 g a.i./ha. In the case of the treatment of seed, the rates of application are from 0.5 g to 1000 g, preferably from 5 g to 100 g, a.i. per 100 kg of seed.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as xylene mixtures or substituted naphthalenes, phthalates, such as dibutyl or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, and vegetable oils or epoxidised vegetable oils, such as epoxidised coconut oil or soybean oil; and water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are e.g. calcite or sand. In addition, a great number of pregranulated materials of inorganic or organic nature can be used, such as especially dolomite or pulverised plant residues.

Depending on the nature of the compounds of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

Especially advantageous application-promoting adjuvants are also natural or synthetic phospholipids from the series of cephalins and lecithins, such as phosphatidylethanolamine, phosphatidylserine, phosphatidylglycerol and lysolecithin.

The agrochemical compositions generally comprise 0.1 to 99%, preferably 0.1 to 95%, of compounds of formulae I and 11, 99.9 to 1%, preferably 99.9 to 5%, of a solid or liquid adjuvant and 0 to 25%, preferably 0.1 to 25%, of a surfactant.

Whereas commercial products will preferably be formulated as concentrates, the end user will normally employ dilute formulations.

The Examples that follow serve to illustrate the invention, "active ingredient" denoting a mixture of compound I and compound II in a specific mixing ratio.

FORMULATION EXAMPLES

| Wettable powders | a) | b) | c) |
|---|---|---|---|
| active ingredient [I:II = 1:3(a), 1:2(b), 1:1(c)] | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (I:IIA:IIB = 1:1:4) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient [I:II = 1:4 (a); 1:5 (b) and 1:1 (c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| active ingredient (I:II = 1:1.5) | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
|---|---|
| active ingredient (I:II = 3:5) | 8% |
| polyethylene glycol (mol. wt. 200) | 3% |
| kaolin | 89% |
| (mol. wt. = molecular weight) | |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:IIA:IIB = 1:2:5) | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% aqueous emulsion) | 1% |
| water | 32% |

The finely ground active ingredient is intimately mixed with the adjuvants, giving a suspension concentrate from which suspensions of any desired dilution can be obtained by dilution with water. Such dilutions can be used to treat living plants and plant propagation material by spraying, pouring or immersion and to protect them against infestation by microorganisms.

BIOLOGICAL EXAMPLES

A synergistic effect exists whenever the action of the active ingredient combination is greater than the sum of the actions of the individual components.

The action E to be expected for a given active ingredient combination, e.g. of two fungicides, obeys the COLBY formula and can be calculated as follows (COLBY, S. R. "Calculating synergistic and antagonistic responses of herbicide combination". Weeds, Vol. 15, pages 20–22; 1967):

ppm=milligram of active ingredient (=ai) per litre of spray mixture $X$=% action by active ingredient I using p ppm of active ingredient $Y$=% action by active ingredient II using q ppm of active ingredient and E=the expected action of active ingredients I+II using p+q ppm of active ingredient (additive action):

$$\text{according to Colby: } E = X + Y - \frac{X \cdot Y}{100}.$$

If the action (O) actually observed is greater than the expected action (E), then the action of the combination is superadditive, i.e. there is a synergistic effect. O/E=synergy factor (SF).

In the Examples that follow, the infestation of the untreated plants is said to be 100%, which corresponds to an action of 0%.

Example 1

Action against Puccinia Recondita on Wheat 7-day-old wheat plants are sprayed to drip point with a spray mixture prepared from a formulation of the active ingredient or active ingredient combination. After 48 hours the treated plants are infected with a conidia suspension of the fungus. The treated plants are then incubated for 2 days at 90–100% relative humidity and 20° C. and placed in a climatic chamber at 21° C. for a further 9 days. 11 days after infection the fungal infestation is assessed. The following results are obtained:

TABLE 1

Compound mixture: IA = epoxiconazol, IIA = propiconazol

| Test No. | mg ai per liter | | | % action found | calculated | Synergy factor SF |
|---|---|---|---|---|---|---|
| | ai IA | ai IIA | I:II | O | E | O/E |
| 0 | — | — | | 0 (control) | | |
| 1 | 0.6 | — | | 0 | | |
| 2 | 2 | — | | 13 | | |
| 3 | — | 0.2 | | 0 | | |
| 4 | — | 2 | | 0 | | |
| 5 | — | 6 | | 35 | | |
| 6 | 0.6 | 0.2 | 3:1 | 13 | 0 | * |
| 7 | 0.6 | 2 | 1:3 | 13 | 0 | * |
| 8 | 2 | 0.2 | 10:1 | 40 | 13 | 3.1 |
| 9 | 2 | 2 | 1:1 | 40 | 13 | 3.1 |

* synergy factor cannot be calculated

Example 2

Action against Erysiphe Graminis on Barley 6-day-old barley plants are sprayed to drip point with a spray mixture prepared from a formulation of the active ingredient or active ingredient combination. After 2 days the plants are inoculated with spores of Erysiphe graminis and incubated in a greenhouse at 21° C. and 60–70% humidity. After 11 days the fungal infestation is assessed. The following results are obtained:

TABLE 2

Compound mixture: IA = epoxiconazol, IIA = propiconazol

| Test No. | mg ai per liter | | | % action found | calculated | SF |
|---|---|---|---|---|---|---|
| | ai IA | ai IIA | I:II | O | E | O/E |
| 0 | — | — | | 0 (control) | | |
| 1 | 0.2 | — | | 0 | | |
| 2 | 0.6 | — | | 0 | | |
| 3 | 2 | — | | 70 | | |
| 4 | — | 0.06 | | 0 | | |
| 5 | — | 0.2 | | 0 | | |
| 6 | — | 0.6 | | 50 | | |
| 7 | — | 2 | | 85 | | |
| 8 | 0.2 | 0.2 | 1:1 | 50 | 0 | * |
| 9 | 0.2 | 0.6 | 1:3 | 65 | 50 | 1.3 |
| 10 | 0.6 | 0.06 | 10:1 | 65 | 0 | * |
| 11 | 0.6 | 0.2 | 3:1 | 65 | 0 | * |
| 12 | 0.6 | 0.6 | 1:1 | 70 | 50 | 1.4 |
| 13 | 2 | 0.2 | 10:1 | 85 | 70 | 1.2 |

* synergy factor cannot be calculated

Examples 3–7/Tab. 3–7

Action against Erysiphe Graminis on Wheat 7-day-old wheat plants are sprayed to drip point with a spray mixture prepared from a formulation of the active ingredient or active ingredient combination. After 1 day the ts are inoculated with spores of Erysiphe graminis and incubated in a greenhouse at 20° C. and 50–80% humidity. After 10 days the fungal infestation is assessed. The flowing results are obtained:

Example 3

TABLE 3

Compound mixture: IB = fenbuconazol, IIA = propiconazol

| Test No. | mg ai per liter | | | % action found | calculated | SF |
|---|---|---|---|---|---|---|
| | ai IB | ai IIA | I:II | O | E | O/E |
| 0 | — | — | | 0 (control) | | |
| 1 | 0.06 | — | | 0 | | |
| 2 | 0.2 | — | | 17 | | |
| 3 | 0.6 | — | | 42 | | |
| 4 | 6 | — | | 48 | | |
| 5 | — | 0.06 | | 10 | | |
| 6 | — | 0.6 | | 13 | | |
| 7 | 0.06 | 0.06 | 1:1 | 60 | 10 | 6 |
| 8 | 0.06 | 0.6 | 1:10 | 55 | 13 | 4.2 |
| 9 | 0.2 | 0.06 | 3:1 | 49 | 25 | 2.0 |
| 10 | 0.2 | 0.6 | 1:3 | 49 | 28 | 1.8 |
| 11 | 6 | 0.6 | 10:1 | 75 | 55 | 1.4 |

Example 4

TABLE 4

Compound mixture: IC = metconazol, IIA = propiconazol

| Test No. | mg ai per liter | | | % action found | calculated | SF |
|---|---|---|---|---|---|---|
| | ai IC | ai IIA | I:II | O | E | O/E |
| 0 | — | — | | 0 (control) | | |
| 1 | 0.06 | — | | 0 | | |
| 2 | 0.2 | — | | 10 | | |
| 3 | 0.6 | — | | 19 | | |
| 4 | 2 | — | | 22 | | |
| 5 | — | 0.6 | | 0 | | |
| 6 | — | 2 | | 64 | | |
| 7 | 0.06 | 0.6 | 1:10 | 17 | 0 | * |
| 8 | 0.2 | 0.6 | 1:3 | 32 | 1 | 32 |
| 9 | 0.2 | 2 | 1:10 | 78 | 64 | 1.2 |
| 10 | 0.6 | 0.6 | 1:1 | 38 | 19 | 2.0 |
| 11 | 2 | 0.6 | 3:1 | 29 | 22 | 1.3 |

* synergy factor cannot be calculated

Example 5

TABLE 5

Compound mixture: ID = tetraconazol, IIA = propiconazol

| Test No. | mg ai per liter | | | % action found | calculated | SF |
|---|---|---|---|---|---|---|
| | ai ID | ai IIA | I:II | O | E | O/E |
| 0 | — | — | | 0 (control) | | |
| 1 | 0.06 | — | | 1 | | |
| 2 | 0.6 | — | | 37 | | |
| 3 | 6 | — | | 47 | | |
| 4 | — | 0.06 | | 10 | | |
| 5 | — | 0.6 | | 13 | | |

TABLE 5-continued

Compound mixture: ID = tetraconazol, IIA = propiconazol

| Test No. | mg ai per liter ai ID | ai IIA | I:II | % action found O | calculated E | SF O/E |
|---|---|---|---|---|---|---|
| 6 | 0.06 | 0.06 | 1:1 | 46 | 11 | 4.2 |
| 7 | 0.06 | 0.6 | 1:10 | 35 | 14 | 2.5 |
| 8 | 6 | 0.6 | 10:1 | 63 | 54 | 1.2 |

Example 6

TABLE 6

Compound mixture: IC = metconazol, IIB = cyprodinil

| Test No. | mg ai per liter ai IC | ai IIB | I:II | % action found O | calculated E | SF O/E |
|---|---|---|---|---|---|---|
| 0 | — | — |  | 0 (control) |  |  |
| 1 | 0.6 | — |  | 32 |  |  |
| 2 | 2 |  |  | 65 |  |  |
| 3 | 6 |  |  | 85 |  |  |
| 4 | — | 2 |  | 8 |  |  |
| 5 | — | 20 |  | 31 |  |  |
| 6 | 0.6 | 2 | 1:3 | 59 | 37 | 1.6 |
| 7 | 0.6 | 20 | 1:30 | 74 | 53 | 1.4 |
| 8 | 2 | 2 | 1:1 | 80 | 68 | 1.2 |
| 9 | 2 | 20 | 1:10 | 84 | 76 | 1.1 |
| 10 | 6 | 2 | 3:1 | 92 | 86 | 1.1 |

Example 7

TABLE 7

Compound mixture: IF = bromuconazol, IIB = cyprodinil

| Test No. | mg ai per liter ai IC | ai IIB | I:II | % action found O | calculated E | SF O/E |
|---|---|---|---|---|---|---|
| 0 | — | — |  | 0 (control) |  |  |
| 1 | 0.1 | — |  | 35 |  |  |
| 2 | 0.25 |  |  | 44 |  |  |
| 3 | 1 | — |  | 46 |  |  |
| 4 | 5 |  |  | 50 |  |  |
| 5 | — | 0.5 |  | 0 |  |  |
| 6 | — | 1 |  | 0 |  |  |
| 7 | 0.1 | 0.5 | 1:5 | 62 | 35 | 1.8 |
| 8 | 0.1 | 1 | 1:10 | 73 | 35 | 2.1 |
| 9 | 0.25 | 0.5 | 1:2 | 54 | 44 | 1.2 |
| 10 | 1 | 0.5 | 2:1 | 56 | 46 | 1.2 |

What is claimed is:

1. A plant microbicidal composition comprising at least two active ingredient components being component I and component II in a synergistically effective amount, together with an inert carrier, wherein said component I is metconazol or a salt or metal complex thereof, and said component II is propiconazol or a salt or metal complex thereof, wherein the weight ratio of component I to component II is in the range of about 1:10 to about 10:1.

2. The composition of claim 1 wherein the ratio of said component I to said component II is 1:3 to 3:1.

3. A method of controlling and preventing the occurrence of fungi on plants, which comprises treating a site infested by or threatened with infestation by fungi with a fungicidally effective amount of a component I which is metconazol or a salt or metal complex thereof, and a component II which is propiconazol or a salt or metal complex thereof, wherein the weight ratio of component I to component II is in the range of about 1:10 to about 10:1, in any desired order or simultaneously.

4. The method of claim 3 wherein cereal is treated.

5. The method of claim 3 wherein a seed is treated.

* * * * *